(12) United States Patent
Witt et al.

(10) Patent No.: US 9,782,692 B2
(45) Date of Patent: Oct. 10, 2017

(54) PREVENTION OF PHASE SEPARATION UPON PROPORTIONING AND MIXING FLUIDS

(75) Inventors: Klaus Witt, Keltern (DE); Konstantin Shoykhet, Karlsruhe (DE)

(73) Assignee: Agilent Technologies, Inc., Santa Clara, CA (US)

( * ) Notice: Subject to any disclaimer, the term of this patent is extended or adjusted under 35 U.S.C. 154(b) by 290 days.

(21) Appl. No.: 14/396,938

(22) PCT Filed: Apr. 25, 2012

(86) PCT No.: PCT/EP2012/057583
§ 371 (c)(1),
(2), (4) Date: Oct. 24, 2014

(87) PCT Pub. No.: WO2013/159816
PCT Pub. Date: Oct. 31, 2013

(65) Prior Publication Data
US 2015/0059451 A1    Mar. 5, 2015

(51) Int. Cl.
*B01D 15/12* (2006.01)
*B01L 3/00* (2006.01)
*G01N 30/34* (2006.01)
*G01N 30/16* (2006.01)

(52) U.S. Cl.
CPC ........ *B01D 15/12* (2013.01); *B01L 3/502784* (2013.01); *G01N 30/16* (2013.01); *G01N 30/34* (2013.01); *B01L 2200/0673* (2013.01); *B01L 2400/0487* (2013.01); *B01L 2400/0644* (2013.01)

(58) Field of Classification Search
CPC ...... G01N 30/34; G01N 30/00; G05D 11/133; B01D 15/12; B01L 3/502784
See application file for complete search history.

(56) References Cited

U.S. PATENT DOCUMENTS

| 4,004,884 A | 1/1977 | Zdrodowski |
| 4,982,597 A | 1/1991 | Berger |
| 5,804,022 A | 9/1998 | Kaltenbach et al. |

(Continued)

FOREIGN PATENT DOCUMENTS

| EP | 0309596 | 4/1989 |
| EP | 1577012 | 9/2005 |

OTHER PUBLICATIONS

International Search Report and Written Opinion mailed Jan. 30, 2013 in International Application No. PCT/EP2012/057583.

(Continued)

*Primary Examiner* — Hezron E Williams
*Assistant Examiner* — David Z Huang (57) ABSTRACT

A fluid supply system configured for supplying fluids includes a fluid packet supply unit configured for controlling supply of a sequence of fluid packets. The fluid packets include a packet of first fluid and a packet of second fluid, wherein the first fluid and the second fluid are media being prone to a phase separation upon direct interaction between the packet of first fluid and the packet of second fluid. The fluid supply system further includes a phase separation inhibiting unit configured for inhibiting phase separation by inserting an intermediate fluid packet between the packet of first fluid and the packet of second fluid.

26 Claims, 3 Drawing Sheets

(56) References Cited

U.S. PATENT DOCUMENTS

| | | | |
|---|---|---|---|
| 2005/0272166 A1* | 12/2005 | Jin | C07H 17/08 |
| | | | 436/94 |
| 2010/0065495 A1* | 3/2010 | Shreve | B01D 15/166 |
| | | | 210/635 |
| 2011/0261642 A1* | 10/2011 | Shreve | G01N 30/34 |
| | | | 366/152.2 |
| 2011/0290042 A1 | 12/2011 | Maeda | |

OTHER PUBLICATIONS

Office action mailed Sep. 30, 2015 in Chinese Application No. 201280072710.4.

* cited by examiner

PREVENTION OF PHASE SEPARATION UPON PROPORTIONING AND MIXING FLUIDS

The present application is a National Stage Application under 35 U.S.C. §371 and claims priority under 35 U.S.C. §121 from International Patent Application No. PCT/EP2012/057583 filed on Apr. 25, 2012. The entire disclosure of international Patent Application No. PCT/EP2012/057583 is specifically incorporated herein by reference.

BACKGROUND

The present invention relates to a fluid supply system, a method of supplying fluids, and a software program or product. The present invention further relates to a sample separation system, in particular a high performance liquid chromatography system, and to a sequence of fluid packets.

In liquid chromatography, a fluidic sample and an eluent (liquid mobile phase) may be pumped through conduits and a column in which separation of sample components takes place. The column may comprise a material which is capable of separating different components of the fluidic analyte. Such a packing material, so-called stationary phase or sorbent which may comprise silica gel, may be filled into a column tube which may be connected to other elements (like a solvent drive unit, containers including sample and/or buffers) by conduits. The composition of the mobile phase can be adjusted by composing the mobile phase from different fluidic components with variable contributions.

In conventional chromatography systems in which multiple fluids are combined to form a solvent composition, undesired interaction between various fluids of the solvent composition may occur which may have a negative impact on the chromatographic performance. For instance, such an undesired interaction may result in the formation of salt crystals. Such salt crystals may deteriorate operation or even destroy components of the chromatography system such as a pump, for instance may result in flow disturbance or even clog an inlet valve of the pump.

SUMMARY

There may be a need for preventing undesired interaction between various fluids of a supplied fluid composition.

According to an exemplary embodiment of the invention, a fluid supply system configured for supplying fluids (such as any liquid, any gas, any mixture of liquid and gas, optionally comprising solid particles) is provided, the fluid supply system comprising a fluid packet supply unit configured for controlling supply of a sequence of fluid packets, the fluid packets comprising a packet of first fluid and a packet of second fluid, wherein the first fluid and the second fluid are media being prone to a phase separation upon direct interaction between the packet of first fluid and the packet of second fluid, and a phase separation inhibiting unit configured for inhibiting phase separation (i.e. the formation of more than one separate phase) by inserting an intermediate fluid packet between the packet of first fluid and the packet of second fluid (thereby particularly spatially separating the first fluid medium from the second fluid medium or transferring at least part of the packets into a diluted state in which phase separation is inhibited or eliminated or at least building an intermediate zone between the packets, for which zone an improved miscibility of the packet components is characteristic).

According to another exemplary embodiment, a sample separation system for separating components of a sample fluid (particularly a sample liquid) in a mobile phase is provided, the sample separation system comprising a fluid supply system having the above-mentioned features, the fluid supply system being configured to drive the fluids as the mobile phase through the sample separation system, and a separation unit, preferably a chromatographic column, configured for separating components of the sample fluid in the mobile phase.

According to another exemplary embodiment of the invention, a sequence of fluid packets is provided, the sequence of fluid packets comprising a plurality of packets of organic solvent, a plurality of packets of buffer, and a plurality of intermediate fluid packets, wherein the packets of organic solvent and the packets of buffer are arranged alternatingly within the sequence of fluid packets, wherein the organic solvent and the buffer are media capable of forming a precipitate (e.g. salt crystals) upon direct interaction with one another, wherein a respective one of the plurality of intermediate fluid packets is interposed between each adjacent pair of a packet of solvent and a packet of buffer.

According to another exemplary embodiment of the invention, a method of supplying fluids, particularly a mixture of fluids, is provided, wherein the method comprises controlling supply of a sequence of fluid packets, the fluid packets comprising a packet of a first fluid and a packet of a second fluid, wherein the first fluid and the second fluid are media capable of forming separate phases (i.e. phase separation) upon direct contact or interaction with one another, and inhibiting formation of separate phases by inserting an intermediate fluid packet at every interface between the packets of first fluid and second fluid.

According to still another exemplary embodiment of the present invention, a software program or product is provided, preferably stored on a data carrier, for controlling or executing the method having the above mentioned features, when run on a data processing system such as a computer (for instance a portable computer, portable data processor or dedicated controller).

Embodiments of the invention can be partly or entirely embodied or supported by one or more suitable software programs, which can be stored on or otherwise provided by any kind of data carrier, and which might be executed in or by any suitable data processing unit. Software programs or routines can be preferably applied in the context of fluid supply control. The fluid supply control scheme according to an embodiment of the invention can be performed or assisted by a computer program, i.e. by software, or by using one or more special electronic optimization circuits, i.e. in hardware, or in form of program stored in non-volatile memory in controlling hardware, that is in form of embedded software, or in hybrid form, i.e. by means of combination of any of the above components. In other words, any implementation in software, firmware (embedded software) and/or hardware (for instance by an ASIC, application specific integrated circuit) is possible.

In the context of this application, the term "fluid packet supply unit" may particularly denote an entity controlling a mode according to which a plurality of fluid packets are to be supplied along a fluidic path or fluid supply line. Such an entity may be a processor such as a microprocessor or a central processing unit (CPU) and may be provided separately from or may be integrally formed with the crystal formation inhibiting unit. The fluid packet supply unit may control switching of a valve which supplies individual fluid packets originating from different fluid containers and/or may control operation of a pump conveying such fluid packets, thereby defining an order according to which fluid packets, which differ regarding their constituents, are forwarded along a fluidic path.

In the context of this application, the term "phase separation inhibiting unit" may particularly denote an entity which controls the supply of the fluid packets under consideration of the boundary condition that undesired formation of a phase separation as a result of a direct interaction between the first and second fluids, particularly salt crystal formation by interaction between an organic solvent and a concentrated buffer, is suppressed or eliminated. For example, the phase separation inhibiting unit may also be a microprocessor of the above type and may be provided separately or integrally formed with the fluid packet supply unit.

In the context of this application, the term "fluid packet" may particularly denote a defined volume of fluid propagating along a fluidic path and being formed of a homogeneous medium.

In the context of this application, the term "intermediate fluid packet" may particularly denote an additional fluid packet which can be intentionally interposed between a preceding fluid packet and a succeeding fluid packet. Such an intermediate fluid packet may be separated from the succeeding and/or preceding fluid packet by phase boundaries, e.g. in the case one of the preceding, intermediate or succeeding packets is gaseous and the other is liquid, or may at least partially intermix with at least one of the preceding fluid packet and the succeeding fluid packet. The intermediate fluid packet is however formed from a completely or at least partially different medium than the preceding fluid packet and the succeeding fluid packet so as to have an influence on the interaction between the preceding fluid packet and the succeeding fluid packet. Hence, the disturbing interaction between preceding fluid packet and succeeding fluid packet may be reduced or excluded by the intermediate fluid packet.

In the context of this application, the term "organic solvent" may particularly denote a solvent which comprises or consists of an organic liquid. Such an organic liquid may for instance be acetonitrile (ACN) or methanol (MeOH). An organic solvent can be used in a sample separation system such as a liquid chromatography system. During a gradient run, an organic solvent may contribute to releasing trapped fractions of a fluidic sample from a chromatographic column.

In the context of this application, the term "buffer" may particularly denote a solution, more particularly an aqueous solution, in which a salt or a salt composition is dissolved to adjust the properties of the buffer. Examples for buffers, particularly for liquid chromatography applications, are potassium formate/formic acid, ammonium acetate, or ammonium hydroxide/ammonia. The skilled person is aware of many other suitable buffers for supporting or optimizing chromatography applications. Such a buffer, for instance diluted with water or any other inorganic solvent, can be used for a sample separation system such as a liquid chromatography system. During a gradient run, a buffer may contribute to conditioning sample components, conditioning the media in a chromatographic column and/or releasing trapped fractions of a fluidic sample from a chromatographic column.

In the context of this application, the term "phase separation" may particularly denote any kind of effect resulting in the formation of an additional phase of the involved fluids, their components or other substances present in the involved fluids or emerging upon their interaction at a boundary between them. As well an emergence of phase boundaries may be denoted as phase separation. The new phase may for instance be a solid phase formed of components of the interacting fluids and may be formed by precipitation. As an example for phase separation, a mixture of the fluids can separate into several liquid phases and/or solid precipitates may be formed; also partial crystallization or gas bubble formation are examples of phase separation.

According to an exemplary embodiment of the invention, a fluid supply system is provided which is less prone for undesired phase separation (such as precipitation of salt crystals) which may conventionally occur at a fluidic (particularly liquid) interface between different fluids (for instance a fluid packet of organic solvent and a directly adjacent fluid packet of concentrated buffer). It has been surprisingly found that such a direct fluidic interface between the different fluids can easily and rapidly result in a phase separation such as precipitation which may then deteriorate the robustness or functionality of the fluid supply system. Based on this cognition, the present invention teaches to interpose one or more intermediate packets between a fluid packet of a first fluid (such as solvent) and a fluid packet of a second fluid (such as buffer) to thereby prevent a direct interaction between these two fluid packets. The intermediate packet may be dimensioned and provided of such a material that the sequence of fluid packets always remains in a phase state in which new phase formation or phase separation (such as precipitation or formation of solid crystals) is safely prevented. Thereby, sensitive components of a fluid supply system such as a fluidic valve or a pump chamber with a reciprocating element may be prevented from failure due to undesired interaction with new phases, particularly with solid phases.

In the following, further exemplary embodiments of the fluid supply system will be explained. However, these embodiments also apply to the sample separation system, the sequence of fluid packets, the method, and the software program or product.

The phase separation inhibiting unit may be configured for preventing a direct contact, particularly a common boundary, between the packet of first fluid and the packet of second fluid. In an embodiment, the phase separation inhibiting unit may be further configured for forming the intermediate fluid packet so that, in view of a remaining indirect interaction between the packet of first fluid and the packet of second fluid, the interacting fluids and/or their components remain within their miscibility or solubility range and outside of a phase separation range. The locations where "remaining indirect interaction" takes place may be in the direction of flow (dynamic locations), but also at an intersection where the flow passes by (static location). The fluid packet supply unit may be configured for bracketing at least one of the packet of first fluid and the packet of second fluid by an assigned pair of a preceding intermediate fluid packet and a succeeding intermediate fluid packet in a supply line such as a fluidic conduit. In one embodiment, the intermediate fluid packet is a diluent for diluting at least a part of at least one of the packet of first fluid and the packet of second fluid to such an extent that phase separation is prevented. The intermediate fluid packet may be configured for maintaining the packet of first fluid spatially separated from the packet of second fluid. At least one of the first fluid and the second fluid is at least one of the group consisting of a pure liquid, a mixture of liquids or solutions, and a solution of solids, liquids and/or gases. The first fluid and the second fluid may be media performing phase separation upon direct interaction between the first fluid and the second fluid due to one of limited miscibility of the first fluid and the second fluid or limited solubility of one of mixture components or solutes in a mixture of the first fluid and the second fluid or in one of the first fluid and the second fluid. In an embodiment, the first fluid is a solvent, particularly an organic solvent, and the second fluid is a buffer.

In an embodiment, the phase separation inhibiting unit may be configured for inhibiting formation of a new phase or of new phase boundaries by inserting the intermediate fluid packet between the packet of first fluid and the packet of second fluid at any of their interfaces. The new phase formation or the formation of new phase boundaries may be at least one of precipitate formation, gel formation, sol formation, suspension formation, emulsion formation, and foam formation.

In an embodiment, the formation of the separate phase is a formation of precipitates, particularly salt crystals.

In an embodiment, it is possible to reliably and continuously supply a mixture of fluids directly from stock solutions such as a first fluid and a second fluid by interlacing a diluting fluid, as the intermediate fluid packet, at any interface location where stock solution, as the first fluid, comes to contact with the second fluid, such as solvent. The mixture may result in a packeted flow stream or in a continuous flow stream. The diluting fluid may be inserted as an extra packet in a packeted stream, as a stream of fluidic layer between the stock solution and the solvent in a continuous coaxial, collateral or otherwise parallel stream, or by extra fork branches in a continuous fork-stream. The interaction between stock solution and solvent may comprise at least one of the group consisting of precipitating, sedimenting, outgasing, forming an emulsion, forming a suspension, forming a foam, forming a gel, forming a sol, reacting in an unwanted or uncontrolled way such as forming unwanted species or intermediates or producing an excess of heat or energy, and producing turbidity.

Next, several embodiments will be described referring to the suppression of salt crystal formation as an example for phase separation, and these embodiments will focus on the first fluid being a buffer and the second fluid being a solvent. However, each of these embodiments can be implemented for other kinds of phase separation differing from salt crystal formation and/or for other kinds of first or second fluids differing from a buffer and a solvent.

In an embodiment, the phase separation inhibiting unit is a crystal formation inhibiting unit, which is configured for preventing a direct contact, particularly for preventing a direct boundary surface, between the packet of first fluid, here embodied as a packet of solvent, and the packet of second fluid, here embodied as a packet of buffer. Hence, when the crystal formation inhibiting unit controls the sequence of the various fluid packets, it ensures that a direct interaction between the medium of the packet of buffer and the medium of the packet of organic solvent is always (i.e. across time) and anywhere (i.e. across location) prevented.

In an embodiment, the crystal formation inhibiting unit is configured for controlling formation of the intermediate fluid packet so that, in view of a remaining indirect (i.e. via another intermediate layer) interaction between the packet of solvent and the packet of buffer, the interacting fluids always remain within a solubility range and outside of a precipitation range. In such an embodiment, constitution of the intermediate fluid packet can be controlled by the crystal formation inhibiting unit in such a way that some interaction between the solvent fluid packet and the buffer fluid packet may remain (for instance due to equilibration, convection or dilution effects), but this interaction may be adjusted to be weak enough so that any precipitation is avoided, retarded or at least reduced. For this purpose, it is possible that phase diagram data (such as data pairs representing one or more curves of a phase diagram indicative of the phase behavior of one or more of components present ab initio or emerging in the mixture) is stored in a database accessible by the crystal formation inhibiting unit. Such a curve may particularly be indicative of a border between a precipitation range and a soluble range in dependence of one or more parameters. Therefore, the intermediate packets may always be statically or even dynamically configured such that the fluidic packet sequence and especially conditions on the boundaries of the packets always remains in the solubility range and never enters the precipitation range.

In an embodiment, the fluid packet supply unit is configured for dimensioning the intermediate fluid packet and/or the packet of buffer and/or the packet of organic solvent to have a volume in a range between about 0.5 µl and about 200 µl, particularly in a range between about 1 µl and about 40 µl, more particularly in a range between about 2 µl and about 10 µl. With these volumes in the order of magnitude of microliters, the fluid supply system may be configured for providing fluid packets suitable for sample separation procedures in a chromatography device such as a liquid chromatography device. The sequence of buffer packet, intermediate packet and solvent packet may be repeated several times with identical or varying volume contributions. During this repetition, the relative amounts of the individual fluid packets may be changed, for instance in a context of a gradient run of a liquid chromatography device.

In an embodiment, the plurality of intermediate fluid packets is configured for preventing a direct contact, particularly a direct boundary surface, between each adjacent pair of a packet of solvent and a packet of buffer. Thereby, it is possible to spatially separate the solvent medium from the buffer medium within the entire sequence of fluid packets. This can be realized by adjusting the chemicals of adjacent fluid packets (for instance, material exchange may be efficiently suppressed by serially conveying firstly a hydrophilic and subsequently a hydrophobic material, or vice versa), by adjusting the phases (for instance by selecting a hardly permeable intermediate packet, for instance from a viscous fluid), etc.

In an embodiment, the fluid packet supply unit is configured for bracketing at least one of the packet of solvent and the packet of buffer by an assigned pair of a preceding intermediate fluid packet and a succeeding intermediate fluid packet in a supply line such as a fluidic conduit. It is hence possible to cover both a front edge and a back edge of the respective packet by medium of the intermediate fluid packet. In such an embodiment, the organic solvent packet is surrounded entirely, i.e. at the front end and at the back end in a fluid propagation direction, with an intermediate fluid packet to ensure that no undesired interaction with other fluid packets, like the buffer, may occur and vice versa.

In an embodiment, the intermediate fluid packet comprises one of a gas bubble, particularly an air bubble, and a liquid packet, particularly water (such as pure water). Thus, the intermediate packet may comprise or consist of different gaseous and/or liquid components and may also comprise solid particles. It is particularly preferred that the intermediate fluid packet is water which can, at an appropriate stage of the fluid handling procedure, be mixed with a concentrated buffer.

In an embodiment, the intermediate fluid packet is a diluent for diluting at least a part of at least one of the packet of solvent and the packet of buffer to such an extent that formation of salt crystals is prevented with the at least one diluent packet. In such an embodiment, the intermediate packet first dilutes the organic solvent and/or the buffer before it contacts the other in order to keep the fluidic system in a solubility range. Diluting the concentrated buffer stock solution (which may be required for certain liquid chromatography applications, for instance during a gradient run) to reduce its salt concentration makes it less likely that undesired salt crystal formation occurs.

In an embodiment, the intermediate fluid packet is configured for maintaining the packet of solvent spatially separated from the packet of buffer. In such an embodiment, the intermediate packet functions as a fluidic spacer which makes any interaction between the solvent fluid packet and the buffer fluid packet impossible. In such an embodiment, the intermediate fluid packet disables, or at least retards fluid communication between solvent fluid packet and buffer fluid packet.

In an embodiment, subsequent ones of the plurality of intermediate fluid packets are dimensioned so that a volume of the preceding intermediate fluid packet related to the total volume of the preceding intermediate fluid packet and a volume of the succeeding intermediate fluid packet is in a range between about 30% and about 70% of that sum, particularly is about 50%. By maintaining the ratio of the volumes of the two consecutive intermediate packets between 3:7 and 7:3, too small volumes of such intermediate fluid packets are avoided. This is advantageous from the point of view of valve switching, since valve switching becomes delicate and challenging when the individual fluid packets have a too small volume.

In an embodiment, the fluid packets may be configured such that an average composition over the entire sequence of the fluid packets or over a sub-sequence of adjacent fluid packets corresponds to a predefined or desired target mixture composition. For instance for a chromatographic separation, a precise composition of solvent and buffer is required for executing a chromatographic method. In other words, an accurately metered predefined target mixture composition should be provided during executing such a chromatographic method. In the described embodiment, the intermediate fluid packets (optionally also the solvent and buffer fluid packets) may be configured so that the resulting fluid composition corresponds to the desired target mixture composition, only the order and the individual volumes of individual packets may be adapted to prevent phase formation. Such an embodiment is not limited to the example of organic solvent and buffer as the first and second fluids, but may be implemented for any kind of first and second fluids being prone to the formation of heterogeneous system or to phase separation upon interaction.

In an embodiment, the fluid supply system is configured for metering fluids, including the solvent and the buffer, in defined proportions and for supplying a resultant mixture, wherein the fluid supply system comprises a plurality of fluid supply lines, each fluidically connected with a fluid source providing a respective fluid, a pumping unit comprising a reciprocating element configured for intaking fluid supplied at an inlet of the pumping unit and for supplying the pressurized fluid at an outlet of the pumping unit, wherein the pumping unit is configured for taking in fluids in defined proportions from selected fluid supply lines and for supplying a pressurized mixture of the fluids at its outlet, and a proportioning valve interposed between the fluid supply lines and the inlet of the pumping unit and being controlled by the fluid packet supply unit and the phase separation inhibiting unit, the proportioning valve configured for modulating solvent composition by sequentially coupling selected ones of the solvent supply lines with the inlet of the pumping unit in the course of the fluid intake phase of the pumping unit. In such embodiments, fluid metering is rendered highly precise, since artifacts resulting from undesired phase separation such as precipitation of salt crystals may be prevented.

In an embodiment, during an intake movement of the reciprocating element, when fluid is drawn in via the inlet of the pumping unit, the proportioning valve performs switching between different solvent supply lines. Therefore, fluid mixing can be performed by switching during the intaking process. It is also possible that, between intervals during which the fluid is drawn in via the inlet of the pumping unit, the proportioning valve performs switching between different solvent supply lines. Hence, the switching may even be performed in time intervals during which the fluid rests.

In an embodiment, the proportioning valve comprises a plurality of switching valves, with some of or all of the switching valves being sequentially actuated during an intake movement of the reciprocating element of the pumping unit. Each of the switching valves may be formed by two switching members, i.e. a stator and a rotor, being rotatable relative to one another for switching.

In an embodiment, the proportioning valve is configured for selecting a selected one of the solvent supply lines corresponding to a multiplexer scheme. In this context, the term "multiplexer" may denote that, at a time, always not more than one of multiple switching valves is coupled to the pumping unit. A multiplexer selects one of several input fluid flows and allows the selected input fluid to flow into a single fluid flow at multiplexer output. It is however particularly possible to connect multiple valves in parallel with multiple sources of the same solvent and to switch the valves simultaneously or in an overlapping manner. This may be advantageous since the flow through multiple valves may have desirable properties so that it may be appropriate to allow the multiple switching valves to be opened at the same time. This however does not conflict with the multiplexing scheme as long as all of the simultaneously operated switching valves dispatch a fluid of the same composition.

In an embodiment, predefined segments of an intake movement of the reciprocating element are assigned to different solvents that are drawn in into the pumping unit, wherein proportioning is done by metering of one of volumetric packets, time slices, and position of the reciprocating element. In this context, a volumetric packet may define a fluid portion having a defined volume. The term "time slices" may denote a certain defined time interval which defines a single phase within a reciprocating element's duty cycle which then, given a defined motion pattern of the reciprocating element, translates into a defined intake volume portion. The position of the reciprocating element in a pumping chamber at the beginning of an intake process as compared to a reference position (for instance a reverse point in a pumping chamber) may also be used as a measure for a fluid amount to be metered. The said volume in a packet, time slice and position of the reciprocating element may be defined, determined or measured directly or indirectly based on calculation such as e.g. calculation of the corresponding commanded motion pattern or on measurement signal of a respective sensor such as flow sensor, volume sensor, pressure sensor, position sensor, rotary or linear position encoder, proximity sensor or alike.

In an embodiment, the pumping unit comprises a further reciprocating element adapted for displacing, in cooperation with the reciprocating element, the fluid supplied at the inlet of the pumping unit and for supplying the fluid further pressurized at the outlet of the pumping unit. In this embodiment, more than one reciprocating element, for instance two pistons, may reciprocate in one and the same pumping chamber. The multiple reciprocating elements may all be controlled as described above for the case of a single reciprocating element only.

In an embodiment, the fluid supply system comprises a further pumping unit arranged downstream of the pumping unit and adapted for displacing, by a further reciprocating element, the fluid supplied at the outlet of the pumping unit and at an inlet of the further pumping unit and for supplying the fluid further pressurized at an outlet of the further pumping unit. In this embodiment, several pumping units with individual reciprocating elements and chambers may be provided. For instance, multiple pumping units may be hydraulically coupled in series. The multiple pumping units may all be controlled in a coordinated manner as described above for the case of a single pumping unit only.

In an embodiment, the reciprocating element comprises a piston, a membrane, or may be adapted as a pressure chamber. However, other embodiments of the reciprocating element are possible as well as long as the reciprocating element is capable of reciprocating within the pumping chamber resulting in reciprocating changes of the volume available to fluid within chamber.

In the following, further exemplary embodiments of the sample separation system will be explained. However, these embodiments also apply to the fluid supply system, the sequence of fluid packets, the method, and the software program or product.

According to embodiments of the present invention, the sample separation system further comprises at least one of: a sample injector configured to introduce the sample into the mobile phase; a detector configured to detect separated components of the sample; a collection unit configured to collect separated components of the sample; a data processing unit configured to process data received from the liquid separation system; a degassing apparatus for degassing the mobile phases; a separating unit such as a chromatographic column for separation of the sample components.

One embodiment of an HPLC system comprises a pumping apparatus having a piston for reciprocation in a pump working chamber to compress liquid in the pump working chamber to a high pressure at which compressibility of the liquid becomes noticeable, and to deliver said liquid at high pressure.

One embodiment of an HPLC system comprises two pumping apparatuses coupled either in a serial or parallel manner. In the serial manner, as disclosed in EP 309596 A1, an outlet of the first pumping apparatus is coupled to an inlet of the second pumping apparatus, and an outlet of the second pumping apparatus provides an outlet of the pump. In the parallel manner, an inlet of the first pumping apparatus is coupled to an inlet of the second pumping apparatus, and an outlet of the first pumping apparatus is coupled to an outlet of the second pumping apparatus, thus providing an outlet of the pump. In either case, a liquid outlet of the first pumping apparatus is phase shifted, preferably essentially 180 degrees, with respect to a liquid outlet of the second pumping apparatus, so that only one pumping apparatus is supplying into the system while the other is intaking liquid (for instance from the supply), thus allowing to provide a continuous flow at the output. However, it is clear that also both pumping apparatuses might be operated in parallel (i.e. concurrently), at least during certain transitional phases for instance to provide a smooth(er) transition of the pumping cycles between the pumping apparatuses. The phase shift might be varied in order to compensate pulsation in the flow of liquid as resulting from the compressibility of the liquid. It is also known to use three piston pumps having about 120 degrees phase shift.

The separating device preferably comprises a chromatographic column providing the stationary phase. The column might be a glass or steel tube (for instance with a diameter from 10 μm to 10 mm and a length of 1 cm to 1 m) or a microfluidic column (as disclosed for instance in EP 1577012 A1 or the Agilent 1200 Series HPLC-Chip/MS System provided by the applicant Agilent Technologies, see for instance http://www.chem.aqilent.com/Scripts/PD-S.asp?IPage=38308). The individual components are retained by the stationary phase differently and separate from each other while they are propagating at different velocities through the column with the eluent. At the end of the column they elute separated, more or less one at a time. During the entire chromatographic process or during certain phases thereof the eluent might be also collected in a series of fractions. The stationary phase or adsorbent in column chromatography usually is a solid material. The most common stationary phase for column chromatography is surface modified silica gel, followed by silica gel and alumina. Cellulose powder has often been used in the past. Known are ion exchange chromatography, reversed-phase chromatography (RP), normal phase chromatography, hydrophilic interaction chromatography, size exclusion chromatography, affinity chromatography etc. The stationary phases are usually fine powders or gels whereas the particles can be partially or entirely meso- and or microporous providing extended surface area. Furthermore, there also exist monolithic columns comprising continuous porous stationary phase body for fast high performance liquid chromatography separations.

The mobile phase (or eluent) can be either a pure solvent or a mixture of different solvents. It can be chosen for instance to adjust the retention of the components of interest and/or to minimize the amount of mobile phase to run the chromatography. The mobile phase can preferably be chosen so that the different components can be separated and/or isolated effectively or selectively like in preparative work. The mobile phase might comprise an organic solvent like for instance methanol or acetonitrile, preferably diluted with water. For gradient operation water and organic solvent may be delivered from separate supply lines or reservoirs, from which the gradient pump delivers a programmed blend to the system. Other commonly used solvents may be isopropanol, tetrahydrofuran (THF), hexane, ethanol or other organic or inorganic liquid components and/or any combination thereof or any combination of these with aforementioned solvents or premixed mixtures comprising any of the aforementioned solvents including water and/or buffer solutions.

The sample liquid might comprise any type of process liquid, natural sample like juice, body liquids like plasma or it may be the result of a reaction like from a fermentation broth.

The fluid is preferably a liquid but may also be or comprise a gas and/or a supercritical fluid (as for instance used in supercritical fluid chromatography—SFC—as disclosed for instance in U.S. Pat. No. 4,982,597 A).

The pressure in the mobile phase might range from 2-200 MPa (20 to 2000 bar), in particular 10-150 MPa (100 to 1500 bar), and more particularly 50-120 MPa (500 to 1200 bar).

BRIEF DESCRIPTION OF DRAWINGS

Other objects and many of the attendant advantages of embodiments of the present invention will be readily appreciated and become better understood by reference to the following more detailed description of embodiments in connection with the accompanying drawings. Features that are substantially or functionally equal or similar will be referred to by the same reference signs. The illustration in the drawing is schematic.

The illustration in the drawing is schematic.

DETAILED DESCRIPTION

The following embodiments will be described referring to suppression of salt crystal formation as an example for phase separation, and these embodiments relate to one fluid being a buffer and another fluid being a solvent. However, each of these embodiments can be implemented for preventing other kinds of phase separation differing from salt crystal formation and/or for other kinds of first or second fluids differing from a buffer and a solvent.

Exemplary embodiments of the invention relate to gradient proportioning in liquid chromatography technology and allow for an improved range of allowed conditions when e.g. a buffer is admixed to an organic solvent. Hence, smart proportioning can be performed to prevent, retard or at least reduce salt crystal formation when the buffer is mixed with the organic solvent.

In High Performance Liquid Chromatography (HPLC) on multi-solvent systems, there may be a requirement to have the flexibility of providing a concentrated buffer in one bottle, a diluent (such as water) in a separate bottle, concentrated or pure organic solvent in a third bottle, and still to allow for an accurate and a precise delivery of a target compositional gradient.

In a regular proportioning scheme with a sequence of all packets in a ring series there is always somewhere a boundary where buffer and organic packets are adjacent. For instance, there may be a sequential intake from a first bottle with water, a second bottle with buffer, and a third bottle with organic solvent (for instance AcN or MeOH). In this case at the buffer-solvent boundary there is direct side-by-side contact of buffer with organic solvent. Such direct connection is risky in a sense that concentrated buffer may diffuse into pure organic solvent, which (at certain positions) may result in an overcritical transient concentration. Precipitate formed may be subsequently dragged to the inlet valve. Undesired results may be a sporadic valve malfunction, a blockage of fluid conduits, etc.

Exemplary embodiments of the invention are based on the consideration that gradient proportioning valves can be controlled in a way such that the water portion is split into at least two packets, so that at any interface of the buffer and organic portions there is water in between. Usually, there is a downside with splitting intake portions. Each valve switching bears a stress, which carries risk and overhead in timing. A convenient result may be a normal control sequence which allows each bottle being connected only once per proportioning ring cycle, taking in the biggest allowed chunk of solvent. Split proportion may help when there is a specific buffer problem or condition. Modern pumps allow to specify the type of solvent, which is offered to the pump intake channels. In case there is water found next to buffer, and both are used to form a diluted buffer being mixed to organic solvent coming from a third channel, then a bigger water portion may be split to a minimum water plug and a remaining plug. These split portions now are arranged before and after for instance the buffer portion to ensure reliable operation. Preferably, this arrangement is not only used in timing, but also in geometry. So the plumbing or channel routing may be done in a special arrangement, as described below in more detail.

Figure 1:
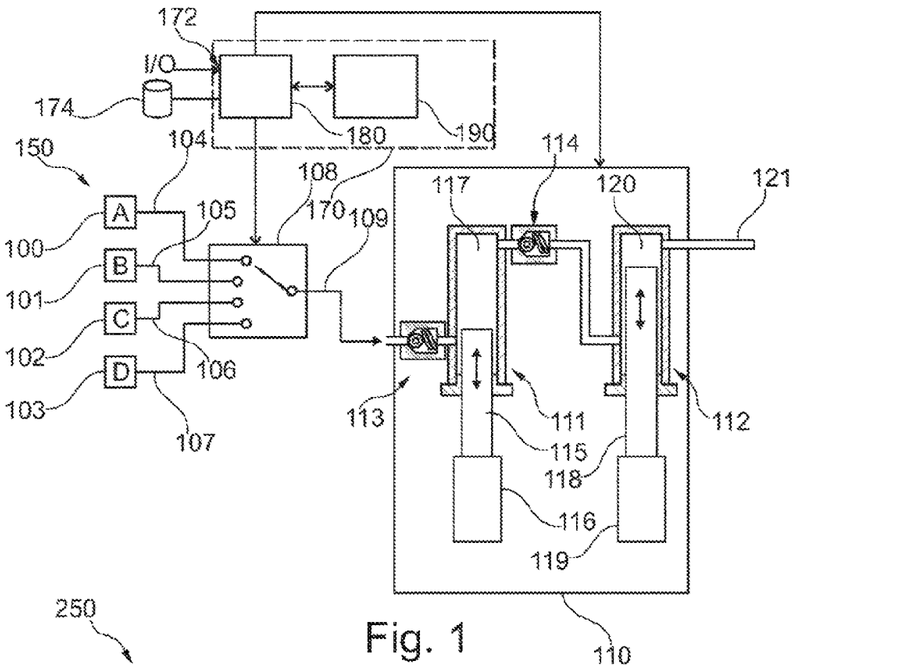
FIG. 1 illustrates a fluid supply system according to an exemplary embodiment of the invention.

FIG. 1 shows a liquid supply system 150 configured for metering liquids in controlled proportions and for supplying a resultant mixture. The liquid supply system comprises four reservoirs 100, 101, 102, 103, with each of the reservoirs containing a respective solvent A (in this example water), B (in this example a buffer, i.e. salt dissolved in a solvent, preferably water), C (in this example organic solvent), D (in this example an optional organic modifier). Each of the reservoirs 100 to 103 is fluidically connected via a respective liquid supply line 104, 105, 106, 107 with a proportioning valve 108. The proportioning valve 108 is configured to connect a selected one of the four liquid supply lines 104 to 107 with a supply line 109, and to switch between different liquid supply lines. The supply line 109 is connected with an inlet of a pumping unit 110. Hence, solvent blending is performed at the low-pressure side of the pumping unit 110 by metering a sequence of fluidic portions.

In the example shown in FIG. 1, the pumping unit 110 comprises a first piston pump 111 fluidically connected in series with a second piston pump 112. The first piston pump 111 is equipped with an inlet valve 113 and with an outlet valve 114. A first piston 115 is driven by a first motor 116 and reciprocates within the first pump chamber 117. A second piston 118 is driven by a second motor 119 and reciprocates within a second pump chamber 120. Alternatively, both pistons 115, 118 can be operated by a common drive system, for instance a differential drive or gear.

During an intake phase of the first piston pump 111, the inlet valve 113 is open, the outlet valve 114 is closed, and the first piston 115 moves in the downward direction. Accordingly, solvent supplied via the supply line 109 is drawn into the first pump chamber 117. During the downward stroke of the first piston 115, the proportioning valve 108 may switch between different liquid supply lines and hence between different solvents. Thus, during the downward stroke of the first piston 115, a sequence of different solvents may be drawn into the first pump chamber 117 one after the other. In an alternative construction, there may be individual inlet valves for each liquid supply line 104 to 107, which then are controlled like and instead of proportioning valve 108.

FIG. 1 furthermore shows that the fluidic valve 108, more particularly the switching performance thereof, is controlled by a processor 170. The processor 170 has two functional blocks denoted with reference numerals 180 and 190 in FIG. 1. However, alternatively to the shown configuration, it is also possible that the reference numerals 180 and 190 are constituted as two separate processors.

The processor 170 comprises a fluid packet supply unit 180 which is configured for controlling switching operation of the fluidic valve 108 so as to supply a defined sequence of fluid packets. The fluid packet supply unit 180 may also be configured for controlling the pumping unit 110 so as to coordinate operation of the fluidic valve 108 and of the pumping unit 110. The fluid packets defined by the fluid packet supply unit 180 comprise packets of organic solvent (constituted by the medium C contained in the third fluid container 102) and fluid packets of buffer (constituted by the medium B contained in the second fluid container 101). The buffer B and the organic solvent C have such chemical properties that their direct interaction may result, under certain operation conditions, in the undesired formation of salt crystals at a liquid boundary between a buffer fluid packet and an organic solvent fluid packet by precipitation. The formation of such salt crystals may deteriorate the function of for instance the inlet valve 113 and of other sensitive components of the fluid supply system 150 of FIG. 1.

In order to suppress such undesired effects, the processor 170 furthermore comprises crystal formation inhibiting unit 190 which is configured for inhibiting formation of the above-mentioned salt crystals by inserting an intermediate fluid packet between each packet of organic solvent and each directly adjacent packet of buffer. As can be taken from FIG. 1, the fluid packet supply unit 180 and the crystal formation inhibiting unit 190 communicate, i.e. may exchange information to carry out a coordinated control scheme for controlling or switching fluidic valve 108.

FIG. 1 furthermore shows that the processor 170 has a bidirectional communication interface 172, i.e. a user interface, by which the processor 170 can communicate with a user. Via the communication interface 172, a user may input commands and may receive output data in accordance with the operation of the fluid supply system 150 of FIG. 1. Moreover, a database 174 can be provided which can be installed on a mass storage device such as a hard disk. The database 174 may comprise information such as data being indicative of a precipitation curve shown in FIG. 11 which can be useful for controlling the fluid supply system 150 of FIG. 1. Particularly, information with regard to precipitation of salt crystals in view of an interaction of the buffer B with the organic solvent C can be stored in the database 174. Since the database 174 is accessible by the processor 170, the fluid supply system 150 can be controlled accordingly.

Figure 2:
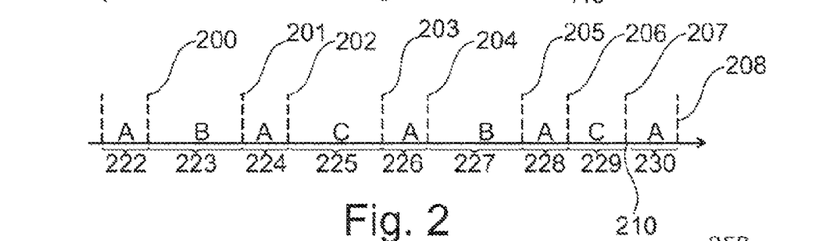
FIG. 2 schematically illustrates a sequence of fluid packets injected with the fluid supply system of FIG. 1.

FIG. 2 shows, plotted along a time axis 210 (which corresponds to a spatial axis along fluidic path 109), a sequence 250 of fluid packets 222 to 230 that can be adjusted by the processor 170 so as to prevent the above described effect of undesired salt formation at certain fluidic interfaces. The sequence 250 comprises an alternating sequence of buffer (B) fluid packets 223, 227 and organic solvent (C) fluid packets 225, 229. However, between each consecutive pair B, C or C, B, a respective intermediate fluid packet 222, 224, 226, 228 of water A is interposed in the sequence 250. These intermediate fluid packets 222, 224, 226, 228 of water A may dilute a packet B and/or C to such an extent that the interaction between the packets B and C is weakened so that no undesired salt formation takes place. Alternatively, fluid packets A may be configured (for instance may comprise a specific fluid, may be dimensioned and/or may be brought to such a temperature and/or pressure) so that they keep consecutive packets B, C separate.

Hence, FIG. 2 shows an example of the three different solvents A, B, C being drawn into the first pump chamber 117 during the downward stroke of a first piston in accordance with a given metering scheme. Initially, the first liquid supply line 104 is connected to the pumping unit's inlet, and solvent A is drawn into the first pump chamber 117 (fluid packet 222). After the first piston 115 has drawn in a certain amount of solvent A, the proportioning valve 108 switches from solvent A to solvent B at a point of time 200. Next, a certain amount of solvent B is drawn in via the second liquid supply line 105 (fluid packet 223). At a point of time 201, the proportioning valve 108 switches from solvent B back to solvent A. Then, a certain, now remaining (with regard to desired total proportion of the fluids A, B, and C in the mixture) amount of solvent A is drawn into the first pump chamber 117 until a point of time 202 (fluid packet 224). Then, a certain amount of solvent C is drawn into the first pump chamber 117 until a point of time 203 (fluid packet 225). Subsequently, further fluid packets 226 to 230 (fluids A-B-A-C-A) are drawn in, wherein switching of the fluidic valve 108 occurs are points of time 204, 205, 206, 207. The point of time 208 indicates the end of the first piston's downward stroke. Thus the resulting repeating proportioning scheme can be denoted as -A-B-A-C-A-B-A-C-A-

During the downward stroke of the first piston 115, the second piston 118 performs an upward stroke and delivers a flow of fluid, and at a pumping unit's outlet 121, a flow of composite solvent at high pressure is provided.

After the respective amounts of different solvents have been drawn into the first pump chamber 117, the inlet valve 113 is shut, the first piston 115 starts moving in the upward direction and compresses the liquid contained in the first pump chamber 117 to system pressure. In an alternative construction, when the proportioning valve 108 is capable to withstand high pressure, an extra inlet valve 113 may be omitted. In this case the line 109 should be shut by the valve 108 at this moment. The outlet valve 114 opens, and during the following solvent delivery phase, the first piston 115 moves in the upward direction, the second piston 118 moves in the downward direction, and the composite solvent is delivered from the first pump chamber 117 to the second pump chamber 120. During this phase, the amount of composite solvent delivered by the first piston pump 111 exceeds the amount of composite solvent drawn in by the second piston pump 112, and hence, at the outlet 125, a continuous flow of composite solvent can be maintained.

After a well-defined amount of composite solvent has been supplied from the first piston pump 111 to the second piston pump 112, the outlet valve 114 is shut, the second piston 118 moves in the upward direction, thus a continuous flow of composite solvent is maintained, while the first piston 115 starts moving in the downward direction, the inlet valve 113 is opened, and again different solvents are drawn into the first pump chamber 117.

Figure 3:
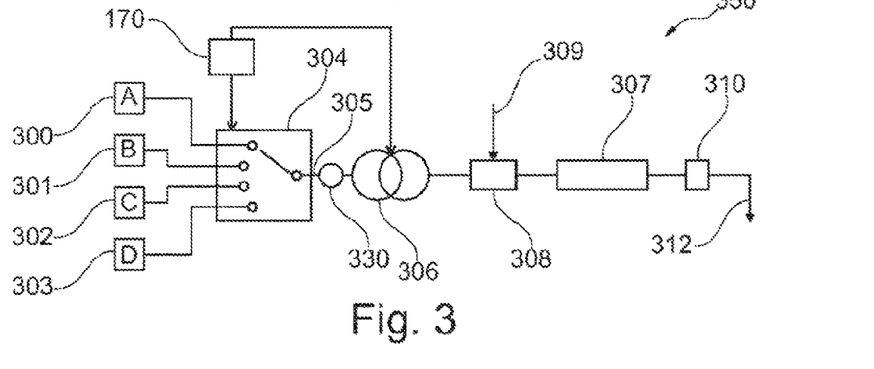
FIG. 3 shows a chromatographic sample separation system according to an exemplary embodiment of the invention.

The fluid supply system 150 shown in FIG. 1 may for example be used for supplying a flow of composite solvent to a sample separation device 350 configured for separating components of a sample liquid. FIG. 3 depicts the setup of such a sample separation system 350. The sample separation system 350 comprises four reservoirs 300 to 303 containing four different solvents A, B, C, D, which are fluidically coupled with a proportioning valve 304. The proportioning valve 304 is responsible for switching between different solvents and for providing the respective solvents to an inlet 305 of the pumping unit 306 at the low-pressure side of the pumping unit. The different solvents are thus brought together at the low pressure side of the pumping unit 306. The pumping unit 306 is configured to supply a flow of composite solvent to a separation device 307, which may for example be a chromatographic column. A sample injector 308 is located between the pumping unit 306 and the separation device 307. By means of the sample injector 308, a sample liquid 309 may be introduced into the separation flow path. The flow of composite solvent supplied by the pumping unit 306 drives the sample through the separation device 307. During passage through the separation device 307, the components of the sample are separated. A detection unit 310 located downstream of the separation device 307 is configured to detect the various components of the sample as they appear at the outlet of the separation device 307.

A mixing unit 330 for mixing the various fluid packets may be located downstream the proportioning valve 304 and upstream the pumping unit 306.

The fluid supply system shown in FIG. 1, FIG. 2 is well-suited for being used in a liquid separation system, for example in a liquid chromatography system. It is to be noted, however, that the fluid supply system shown in FIG. 1 may be used in other fields as well. According to an exemplary embodiment of the invention, smart proportioning of fluid packets can be performed to prevent, retard or at least reduce phase separation, more specifically prevent salt crystal formation when a buffer is mixed with an organic solvent.

Figure 4:
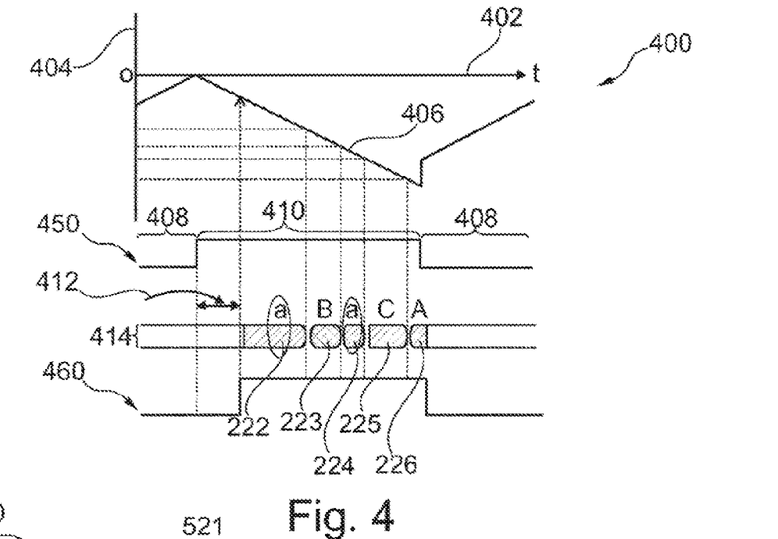
FIG. 4 is a schematic diagram illustrating a switching cycle of a multiplexing fluidic valve and a sequence of fluid packets according to an exemplary embodiment of the invention.

FIG. 4 shows a diagram 400 illustrating a switching performance of a valve such as valve 108 in combination with a reciprocation performance of the piston 115 or 118. Along an abscissa 402 of the diagram 400, the time is plotted. Along an ordinate 404, the piston position is plotted. The ordinate value "0" indicates an upper dead point of the piston movement with regard to e.g. FIG. 1, and a lower dead point of the piston is defined by the minimum of curve 406 and is plotted in FIG. 4 as well. A rectangular trace 450 in FIG. 4 shows intake (upper level) and delivery (lower level) phases as logical levels. Reference numeral 408 indicates a delivery state, reference numeral 410 indicates an intake phase. Reference numeral 412 indicates a decompression volume. Curve 460 shows the solvent inflow. It also indicates the state of the inlet valve 113, the inlet valve being either in an open state (the upper logical value) or in a closed state (the lower logical value). When the channel is open, see reference numeral 414, the individual fluid packets 222 to 226 are sequentially supplied along the fluid supply path 109 of FIG. 1. As can be taken from FIG. 4, a bigger water portion (A) may be split to a first water plug (a) and a remaining plug (a) along with terminating plug A (226). One split proportion (a) now is arranged before the buffer portion B, and the other one (a) is arranged after the buffer portion (B) to ensure reliable operation and to prevent direct contact between fluid packets 223 and 225 (buffer B and solvent C). The FIG. 4 represents now a solvent proportioning scheme of type -A-B-A-C-A-.

Figure 5:
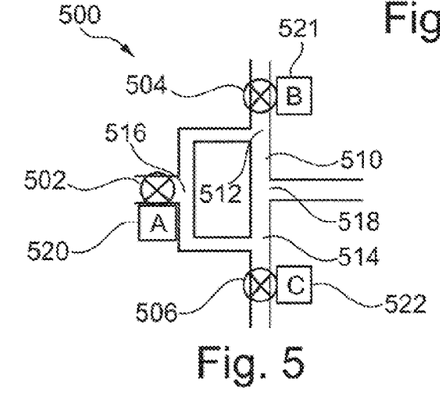
FIG. 5 illustrates a fluid handling unit in which various fluids are brought in interaction prior to entering a common conduit for preventing undesired salt crystal formation due to an interaction of the different fluids.
Figure 6:
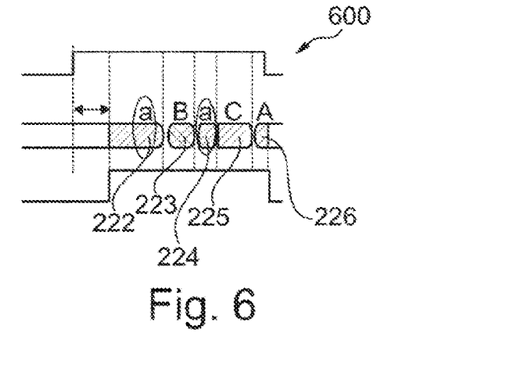
FIG. 6 illustrates a sequence of fluidic packets as obtained according to the scheme of FIG. 5.

FIG. 5 shows a fluid handling unit 500 (such as a flow joiner or junction, mixing unit, proportioning unit, solvent blending unit, solvent-mix generator, etc.) for bringing water A from a container when valve 502 is activated in interaction with buffer B from a container when valve 504 is activated and solvent C from a container when valve 506 is activated. Various T-points 512, 514, 516, 518 are shown in FIG. 5 at which the various components A, B, C are mixed. The fluid handling can be controlled by valves 502, 504, 506 controlling the respective supply of the components A, B, C. With the switching scheme illustrated in FIG. 6, the sequence 600 of fluid packets denoted with reference numerals 222 to 226 can be obtained. With this sequence, undesired interaction between components B and C particularly at the T-points 512, 514, 516 can be avoided.

Figure 7:
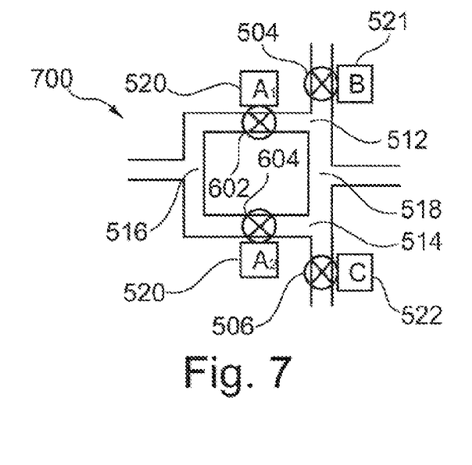
FIG. 7 illustrates another fluid handling unit in which various fluids are brought in interaction prior to preventing undesired salt crystal formation due to an interaction of different fluids.
Figure 8:
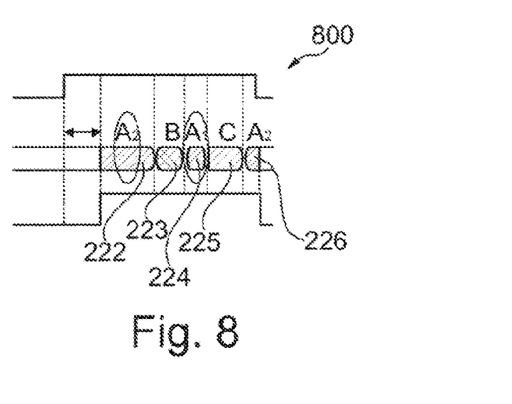
FIG. 8 illustrates a sequence of fluidic packets as obtained according to the scheme of FIG. 7.

FIG. 7 shows an alternative fluid handling unit 700 which differs from FIG. 5 particularly in that water is supplied via two channels denoted with reference numerals A1, A2. Consequently, two valves 602, 604 are provided instead of one valve 502 in FIG. 5. FIG. 8 shows a corresponding sequence 800 of fluid packets 222 to 226, compare reference numerals A1 and A2 for the respective fluid packets of water originating from the respective containers 100.

Figure 9:
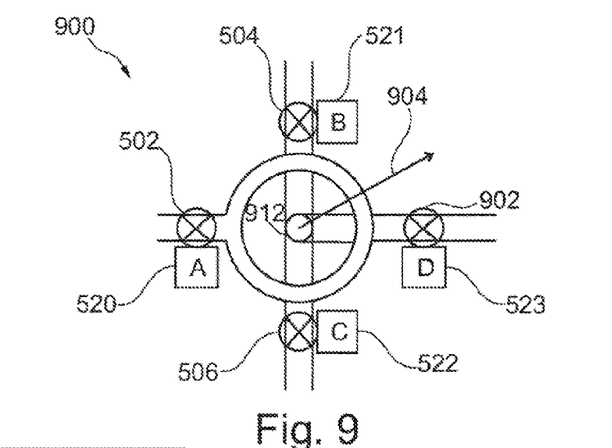
FIG. 9 illustrates still another fluid handling unit in which various fluids are brought in interactions prior to entering a common conduit for preventing undesired salt crystal formation due to an interaction of different fluids.
Figure 10:
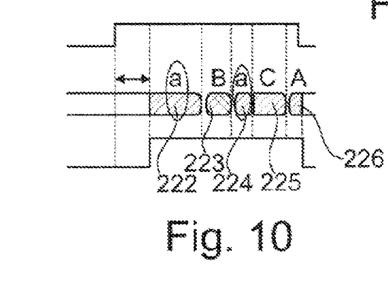
FIG. 10 illustrates a sequence of fluidic packets as obtained according to the scheme of FIG. 9.

A fluid handling unit 900 according to another exemplary embodiment of the invention is shown in FIG. 9. Here, also a component D in a container when valve 902 is activated is included in the mixing which renders a further valve 902 necessary. Fluid D can be an organic modifier and is optional. With the configuration of FIG. 9, the components can be brought in interaction at a point 912 and can be supplied via an outlet line 904. This results in the formation of the sequence 1000 of fluid packets 222 to 228 (only a part thereof is shown in FIG. 10).

Figure 11:
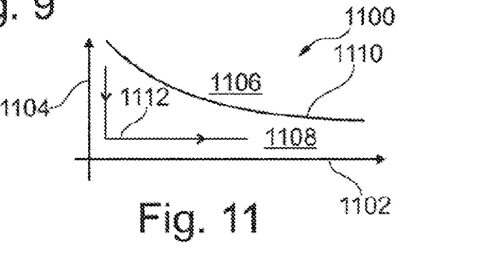
FIG. 11 shows a diagram illustrating a curve delimiting a precipitation range from a solubility range of a mixture of different fluids.

FIG. 11 shows a diagram 1100 illustrating a miscibility diagram with axes representing an organic content, see abscissa 1102, and a buffer molarity, see ordinate 1104 of a mixture of buffer B and organic solvent C. A curve 1110 separates a precipitation range 1106 from a solubility range 1108. Within the precipitation range 1106, undesired formation of salt crystals may occur, wherein the mixture remains in a completely soluble phase within the soluble range 1108. For instance, an exemplary embodiment of the invention may ensure that the system is driven or controlled along a trajectory 1112 or similar trajectories which remain always within the soluble range 1108 preferably at any point in space and time. This can be adjusted by a corresponding provision of intermediate packets.

Figure 12:
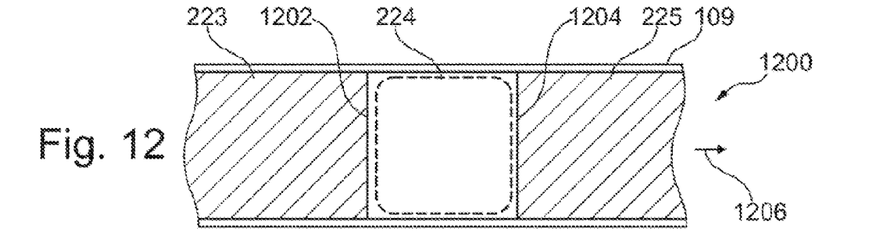
FIG. 12 illustrates a sequence of fluid packets according to an exemplary embodiment of the invention propagating within a fluidic conduit, wherein a packet of buffer and a packet of solvent are spatially separated from one another by an air bubble.

FIG. 12 illustrates a sequence 1200 of fluid packets according to an exemplary embodiment of the invention propagating along a fluidic conduit 109 in a propagation direction 1206. In this embodiment, a packet of buffer 223 and a packet of solvent 225 are spatially separated from one another by an air bubble 224. The intermediate air bubble 224 maintains the packet of solvent 225 spatially separated from the packet of buffer 223. Consequently, no undesired salt formation may occur, since there is no direct fluidic interface between the packet of solvent 225 and the packet of buffer 223.

Figure 13:
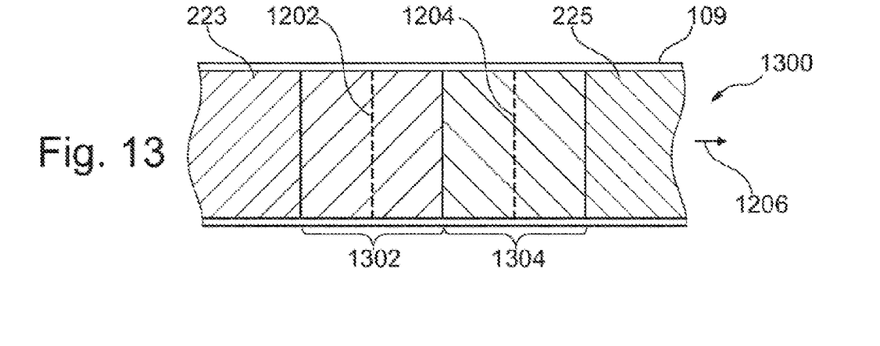
FIG. 13 illustrates a sequence of fluid packets according to another exemplary embodiment of the invention propagating within a fluidic conduit, wherein diluent fluid sections are arranged between a packet of concentrated buffer and a packet of solvent.

FIG. 13 illustrates a sequence of fluid packets according to another exemplary embodiment of the invention propagating along fluidic conduit 109 in propagation direction 1206. A first diluted fluid section 1302 resulting from a mixture between a front edge of packet of concentrated buffer 223 and a back edge of an intermediate packet of water (no longer visible in FIG. 13) and a second diluted fluid section 1304 resulting from a mixture between a front edge of the intermediate packet of water 224 and a back edge of a packet of solvent 225 are arranged between remaining sections of pure concentrated buffer 223 and pure solvent 225. Consequently, no undesired salt crystal formation may occur, since the packet of solvent 225 and the packet of buffer 223 have been diluted with water in an adjacent volume range so as to remain outside of the precipitation range (see reference numeral 1106 in FIG. 11).

It should be noted that the term "comprising" does not exclude other elements or features and the term "a" or "an" does not exclude a plurality. Also elements described in association with different embodiments may be combined. It should also be noted that reference signs in the claims shall not be construed as limiting the scope of the claims.

The invention claimed is:

1. A liquid supply system configured to supply liquids, the liquid supply system comprising:
    a plurality of liquid supply lines, each fluidically connected with a liquid source providing a respective liquid;
    a pumping unit comprising an inlet and an outlet, the pumping unit configured to intake liquids at the inlet in defined proportions from selected ones of the liquid supply lines and to supply a pressurized mixture of the liquids at the outlet;
    a proportioning valve interposed between the liquid supply lines and the inlet of the pumping unit, the proportioning valve configured to modulate solvent composition by sequentially coupling the selected ones of the liquid supply lines with the inlet of the pumping unit while the pumping unit is intaking liquids;
    a liquid packet supply unit configured to control the proportioning valve to supply the liquids from the selected ones of the liquid supply lines as of a sequence of liquid packets, the liquid packets comprising a packet of first liquid and a packet of second liquid, wherein the first liquid and the second liquid are media capable of forming separate phases upon direct interaction with each other; and
    a phase separation inhibiting unit configured to communicate with the liquid packet supply unit to inhibit the forming of separate phases by inserting an intermediate liquid packet between the packet of first liquid and the packet of second liquid.

2. The liquid supply system according to claim 1, wherein the phase separation inhibiting unit is configured to prevent a direct contact between the packet of first liquid and the packet of second liquid.

3. The liquid supply system according to claim 1, wherein the phase separation inhibiting unit is configured to form the intermediate liquid packet so that, in view of a remaining indirect interaction between the packet of first liquid and the packet of second liquid, the interacting liquids remain within a miscibility or solubility range of the interacting fluids and outside of a phase separation range of the interacting liquids.

4. The liquid supply system according to claim 1, wherein the liquid packet supply unit is configured to dimension at least one of the intermediate liquid packet, the packet of first liquid or the packet of second liquid to have a volume in a range between 0.5 µl and 200 µl.

5. The liquid supply system according to claim 1, wherein the liquid packet supply unit is configured for bracketing at least one of the packet of first liquid or the packet of second liquid by an assigned pair of a preceding intermediate liquid packet and a succeeding intermediate liquid packet in a supply line.

6. The liquid supply system according to claim 1, wherein the intermediate liquid packet is a diluent for diluting at least a part of at least one of the packet of first liquid or the packet of second liquid to such an extent that phase separation is prevented.

7. The liquid supply system according to claim 1, wherein the intermediate liquid packet is configured to maintain the packet of first liquid spatially separated from the packet of second liquid.

8. The liquid supply system according to claim 1, comprising a feature selected from the group consisting of:
    at least one of the first liquid or the second liquid is one selected from the group consisting of a pure liquid; a mixture of liquids or solutions; and a solution of solids, liquids, or a combination of two or more of solids, liquids or gases;
    the first liquid and the second liquid are media performing phase separation upon direct interaction between the first liquid and the second liquid due to one of limited miscibility of the first liquid and the second liquid or limited solubility of one of mixture components or solutes in a mixture of the first liquid and the second liquid or in one of the first liquid and the second liquid;
    the first liquid is a solvent;
    the second liquid is a buffer;
    the first liquid and the second liquid are media capable of forming salt crystals upon direct interaction between the packet of first liquid and the packet of second liquid;
    the first liquid and the second liquid upon their contact are capable of undergoing a chemical transformation resulting in a heterogeneous mixture;
    the first liquid and the liquid fluid upon their contact are capable of undergoing an undesired or uncontrolled chemical reaction;
    the phase separation inhibiting unit is a crystal formation inhibiting unit configured to inhibit crystal formation by inserting the intermediate liquid packet between the packet of first liquid and the packet of second liquid;
    the phase separation inhibiting unit is configured to inhibit formation of a new phase or of new phase boundaries by inserting the intermediate liquid packet between the packet of first liquid and the packet of second liquid;
    the phase separation inhibiting unit is configured to inhibit formation of a new phase by inserting the intermediate liquid packet between the packet of first liquid and the packet of second liquid, wherein the new phase formation is at least one of precipitate formation, gel formation, sol formation, or suspension formation;
    the phase separation inhibiting unit is configured to inhibit formation of new phase boundaries by inserting the intermediate liquid packet between the packet of first liquid and the packet of second liquid, wherein the formation of new phase boundaries is at least one of emulsion formation or foam formation; and
    a combination of two or more of the foregoing.

9. The liquid supply system according to claim 1, further comprising a feature selected from the group consisting of:
  the pumping unit comprises a reciprocating element configured to intake the liquid supplied at the inlet of the pumping unit and to supply the pressurized liquid at the outlet of the pumping unit;
  during intaking liquid, when liquid is drawn in via the inlet of the pumping unit, or between intervals during which the liquid is drawn in via the inlet of the pumping unit, the proportioning valve performs switching between different liquid supply lines;
  the proportioning valve comprises a plurality of switching valves, with the switching valves being sequentially actuated during an intake movement of a reciprocating element of the pumping unit;
  the proportioning valve comprises at least one multi-port selection valve;
  the proportioning valve is configured to select a selected one of the liquid supply lines corresponding to a multiplexer scheme;
  predefined portions of an intake movement of a reciprocating element are assigned to different solvents that are drawn into the pumping unit, wherein proportioning is done by metering of one of volumetric packets, time slices, or position of the reciprocating element;
  the pumping unit comprises a further reciprocating element configured to displace, in cooperation with a first reciprocating element, the liquid supplied at the inlet of the pumping unit—and to supply the liquid further pressurized at the outlet of the pumping unit;
  the liquid supply system comprises a further pumping unit arranged downstream of the pumping unit and configured to displace, by a further reciprocating element, the liquid supplied at the outlet of the pumping unit and at an inlet of the further pumping unit and to supply the liquid further pressurized at an outlet of the further pumping unit;
  the liquid supply system comprises a further pumping unit arranged hydraulically parallel to the pumping unit and configured to displace by a further reciprocating element in alternating manner together with the pumping unit, the liquid supplied from the proportioning valve; and
  a combination of two or more of the foregoing.

10. A sample separation system to separate components of a sample liquid in a mobile phase, the sample separation system comprising:
  a liquid supply system according to claim 1, the liquid supply system being configured to drive the liquids as the mobile phase through the sample separation system; and
  a separation unit configured to separate components of the sample liquid in the mobile phase.

11. The sample separation system of claim 10, further comprising a feature selected from the group consisting of:
  a sample injector configured to introduce the sample liquid into the mobile phase;
  a detector configured to detect separated components of the sample liquid;
  a collection unit configured to collect separated components of the sample liquid;
  a data processing unit configured to process data received from the sample separation system;
  a degassing apparatus configured to degas the mobile phase; and
  a combination of two or more of the foregoing.

12. A method of supplying liquids, the method comprising:
  operating a pumping unit comprising an inlet and an outlet to intake liquids at the inlet in defined proportions from selected ones of a plurality of liquid supply lines and to supply a pressurized mixture of the liquids at the outlet, the liquid supply lines each fluidically connected with a liquid source providing a respective fluid;
  operating a proportioning valve, interposed between the liquid supply lines and the inlet of the pumping unit, to modulate solvent composition by sequentially coupling the selected ones of the liquid supply lines with the inlet of the pumping unit while the pumping unit is intaking liquids;
  controlling the proportioning valve to supply the liquids from the selected ones of the liquid supply lines as a sequence of liquid packets, the liquid packets comprising a packet of a first liquid and a packet of a second liquid, wherein the first liquid and the second liquid are media capable of forming separate phases upon direct interaction with each other; and
  inhibiting formation of a new separate phase by inserting an intermediate liquid packet at at least one interface between the packets of first liquid and second liquid.

13. The method of claim 12, wherein the formation of the new separate phase is a formation of precipitates.

14. The method of claim 12, wherein the intermediate liquid packet is a diluting liquid.

15. The method of claim 12, wherein inserting the intermediate liquid packet results in a packeted flow stream or in a continuous flow stream.

16. The method of claim 14, wherein the diluting liquid is inserted as an additional packet in a packeted stream, as a stream of fluidic layer between the first liquid and the second liquid in a continuous coaxial stream, or by extra fork branches in a continuous fork-stream.

17. The method of claim 12, wherein an interaction between the first liquid and the second liquid is selected from the group consisting of: precipitating, sedimenting, outgasing, forming an emulsion, forming a suspension, forming a foam, forming a gel, forming a sol, causing a reaction unwanted in the method, producing an excess of heat or energy, and producing turbidity.

18. The method of claim 12, wherein inhibiting formation of a new separate phase by inserting the intermediate liquid packet is performed by consideration of phase or miscibility diagrams for a system of the first liquid, the second liquid and a third liquid, the third liquid constituting the intermediate liquid packet.

19. The method of claim 12, wherein, in the sequence of liquid packets, the first liquid is an organic solvent and the second liquid is a buffer, and
  the organic solvent and the buffer are media capable of forming precipitate upon direct interaction with each other.

20. The method of claim 12, wherein the intermediate liquid packet is configured to prevent a direct contact between the packet of the first liquid and the packet of the second liquid.

21. The method of claim 19, wherein at least a part of the intermediate liquid packet comprises a diluent for diluting the organic solvent, the buffer, or both the organic solvent and the buffer, to such an extent that formation of salt crystals is prevented between the packet of the first liquid and the packet of the second liquid.

22. The method of claim 12, wherein at least a part of the intermediate liquid packet is configured to maintain the packet of the first liquid and the packet of the second liquid spatially separated from each other.

23. The method of claim 12, wherein at least one of the intermediate liquid packet, the packet of the first liquid, or the packet of the second liquid has a volume in a range between 1 µl and 200 µl.

24. The method of claim 12, wherein:
- the sequence of liquid packets comprises a plurality of packets of the first liquid, a plurality of packets of the second liquid, and a plurality of packets of the intermediate liquid, with the packets of the first liquid and the packets of the second liquid are arranged alternatingly, and the packets of the intermediate liquid inserted between respective adjacent pairs of the packets of the first liquid and the packets of the second liquid; and
- subsequent ones of the plurality of intermediate liquid packets are dimensioned so that a volume of the preceding intermediate liquid packet divided by the volume of the preceding intermediate liquid packet plus a volume of the succeeding intermediate liquid packet is in a range between 30% and 70%.

25. The method of claim 12, wherein:
- the sequence of liquid packets comprises a plurality of packets of the first liquid, a plurality of packets of the second liquid, and a plurality of packets of the intermediate liquid, with the packets of the first liquid and the packets of the second liquid are arranged alternatingly, and the packets of the intermediate liquid inserted between respective adjacent pairs of the packets of the first liquid and the packets of the second liquid; and
- the sequence of fluid packets is configured such that an average composition over the entirety of the liquid packets corresponds to a predefined target mixture composition.

26. A non-transitory computer readable medium storing a program, executable by a controller, for executing a method according to claim 12.

* * * * *